United States Patent
Takahashi et al.

(10) Patent No.: US 7,711,217 B2
(45) Date of Patent: May 4, 2010

(54) ACTIVE SENSOR, MULTIPOINT ACTIVE SENSOR, METHOD FOR DIAGNOSING DETERIORATION OF PIPE, AND APPARATUS FOR DIAGNOSING DETERIORATION OF PIPE, AND APPARATUS FOR DIAGNOSIS DETERIORATION OF PIPE

(75) Inventors: Masashi Takahashi, Yokohama (JP); Keiichi Sasaki, Tokyo (JP); Nobuo Yamaga, Tokyo (JP); Norio Ahiko, Yokohama (JP); Koichi Yoshimura, Yokohama (JP); Masanobu Ohi, Tokyo (JP); Yoshio Mochida, Ebina (JP); Yuuichi Machijima, Tokyo (JP); Takehiro Shirai, Ichihara (JP)

(73) Assignees: Kabushiki Kaisha Toshiba, Tokyo (JP); Lazoc Incorporated, Tokyo (JP)

( * ) Notice: Subject to any disclaimer, the term of this patent is extended or adjusted under 35 U.S.C. 154(b) by 0 days.

(21) Appl. No.: 12/101,395

(22) Filed: Apr. 11, 2008

(65) Prior Publication Data
US 2008/0260324 A1    Oct. 23, 2008

(30) Foreign Application Priority Data
Apr. 13, 2007  (JP) ............................. 2007-106025

(51) Int. Cl.
*G02B 6/00* (2006.01)
*G01B 11/02* (2006.01)
*G21C 17/017* (2006.01)

(52) U.S. Cl. ............................ 385/12; 385/13; 356/465; 356/503; 356/630; 702/183

(58) Field of Classification Search ................... 385/12, 385/13; 356/73.1, 465, 485, 503, 630, 901, 356/908; 702/183
See application file for complete search history.

(56) References Cited

U.S. PATENT DOCUMENTS

| | | | |
|---|---|---|---|
| 5,513,533 A | * | 5/1996 | Wheeler et al. ............... 73/657 |
| 5,811,682 A | | 9/1998 | Ohtani et al. |
| 5,886,521 A | * | 3/1999 | Hassan ....................... 324/227 |
| 7,262,834 B2 | | 8/2007 | Kageyama et al. |

FOREIGN PATENT DOCUMENTS

| | | |
|---|---|---|
| JP | 3517699 | 2/2004 |
| WO | WO 03/002956 A1 | 1/2003 |

* cited by examiner

*Primary Examiner*—Daniel Petkovsek
(74) *Attorney, Agent, or Firm*—Oblon, Spivak, McClelland, Maier & Neustadt, L.L.P.

(57) ABSTRACT

An active sensor 10 is positioned on an outside of a pipe 60 so as to detect a thickness of the pipe. The active sensor comprises: an oscillator 15 capable of inputting oscillatory waves into the pipe and sweeping a frequency of the oscillatory waves within a desired range; and an optical fiber sensor mounted on the pipe, the optical fiber sensor detecting the oscillatory waves generated in the pipe.

19 Claims, 13 Drawing Sheets

ACTIVE SENSOR, MULTIPOINT ACTIVE SENSOR, METHOD FOR DIAGNOSING DETERIORATION OF PIPE, AND APPARATUS FOR DIAGNOSING DETERIORATION OF PIPE, AND APPARATUS FOR DIAGNOSIS DETERIORATION OF PIPE

CROSS REFERENCE TO RELATED APPLICATIONS

This application is based upon and claims the benefit of priority from the prior Japanese Patent Application No. 2007-106025 filed on Apr. 13, 2007, the entire contents of which are incorporated herein by reference.

BACKGROUND OF THE INVENTION

1. Field of the Invention

The present invention relates to an active sensor, a multi-point active sensor, a method of diagnosing deterioration of a pipe, and an apparatus for diagnosing deterioration of a pipe, capable of judging existence of a malfunction such as a pipe wall-thickness reduction caused by a high-temperature steam in an atomic power plant and a heat power plant, and a pipe corrosion in a chemical factory and an incineration plant, and capable of identifying the part having a trouble.

2. Description of Related Art

A pipe wall-thickness reduction and a pipe corrosion are conventionally inspected on periodic inspections by using an ultrasonic flaw detecting method and an X-ray transmission method. In the ultrasonic flaw detecting method, a probe that transmits and receives ultrasonic waves is brought into contact with a surface of a pipe, for example, and ultrasonic waves of various frequencies are propagated to an inside (pipe wall part) of the pipe. Then, by receiving the ultrasonic waves that have been reflected on a flaw in the pipe wall part of the pipe or a rear surface of the pipe and returned therefrom, a state of the pipe wall part of the pipe can be grasped.

A position of the flaw can be obtained by measuring a time period between the transmittance of the ultrasonic waves and the reception thereof. A size of the flaw can be obtained by measuring a height of the received echo (intensity of the ultrasonic waves that have been reflected and returned) and a range where the echo appears.

Such an ultrasonic flaw detecting method is mainly used in an atomic power plant, for detecting a plate thickness and a lamination (side cutting appearing in a cut surface of the plate) of a material, and detecting a fusion deficiency of a fused part and a base material by welding, and a crack generated in a thermally affected part. In addition, with respect to a build up welding for reinforcing a nozzle opening, a branch, and a pipe joint, which are disposed around a pressure vessel of an atomic reactor, the ultrasonic flaw detecting method is applied to a base material directly below a build-up welded part, a fused part, and a build-up deposited part (see, Atomic Energy and Design Technique, Okawa Shuppan, (1980), pp. 226 to 250 (Giitiro Uchigasaki, et al.)).

On the other hand, the X-ray transmission method can detect a pipe wall-thickness reduction, without detaching a heat insulation material from the pipe. In the X-ray transmission method, data, which haven been provided by a serial radiographic apparatus such as an X-ray CT scanner, are subjected to a high-speed image processing by using a powerful computer, so as to make an image of the overall object with a fault image showing different X-ray transmittances.

Recently, there is known a method capable of simultaneously taking a picture of substances of different X-ray transmittances, by a simple system including only a sheet-like color scintillator (fluorescent screen) and a CCD camera. The color scintillator emits three primary colors of light, i.e., red (R), green (G), and blue (B), with a luminescent ratio changing in accordance with a transmission amount. This method is used for observing a pipe wall-thickness reduction and for inspecting foreign matters in a thermal/atomic power plant and an oil/chemical complex.

However, in the above ultrasonic flaw detecting method, it is necessary to measure the thickness of a pipe at not less than 1000 positions, and thus it is difficult to conduct the method during a periodic inspection. Further, when the thickness of the pipe is measured, it is necessary to stop the plant in consideration of a temperature constraint, which results in decrease in availability factor.

On the other hand, in the X-ray method capable of detecting a malfunction through the heat insulation member of the pipe, although the method can measure a distribution of the thickness of the pipe, the method is not widely used because an apparatus therefor is expensive.

SUMMARY OF THE INVENTION

The present invention has been made in view of the above circumstances. The object of the present invention is to provide an active sensor, a multi-point active sensor, a method of diagnosing deterioration of a pipe, and an apparatus for diagnosing deterioration of a pipe, capable of inspecting, while a plant is running, a pipe over a wide area thereof for a short period of time, and of reducing the time and the number of steps required for the inspection, at a low manufacturing cost.

The present invention is an active sensor positioned on an outside of a pipe so as to detect a thickness of the pipe, the active sensor comprising: an oscillator capable of inputting oscillatory waves into the pipe and scanning a frequency of the oscillatory waves within a desired range; and an optical fiber sensor mounted on the pipe, the optical fiber sensor detecting the oscillatory waves generated in the pipe.

Due to this structure, there can be obtained, at a low manufacturing cost, a thin active sensor capable of simply inspecting a pipe while a plant is running, and of significantly reducing the time and the number of steps required for the inspection.

The present invention is an active sensor positioned on an outside or an inside of a pipe so as to detect a thickness of the pipe, the active sensor comprising: an oscillator capable of inputting oscillatory waves into the pipe and scanning a frequency of the oscillatory waves over a desired range; and an optical fiber sensor mounted on the pipe, the optical fiber sensor detecting the oscillatory waves generated in the pipe.

Due to this structure, there can be obtained, at a low manufacturing cost, a thin active sensor capable of simply inspecting a pipe while a plant is running, and of significantly reducing the time and the number of steps required for the inspection.

The present invention is a multi-point active sensor comprising the plurality of aforementioned active sensors wherein the active sensors are linearly arranged or arranged in matrix.

Due to this structure, the thickness of the pipe can be measured and mapped over a wider area, whereby the malfunction of the pipe can be accurately detected.

The present invention is a method of diagnosing deterioration of a pipe using the aforementioned multi-point active sensor, the method comprising the steps of: inputting oscillatory waves into a pipe by the oscillator of at least one active sensor; detecting the oscillatory waves generated in the pipe by the optical fiber sensor of at least one active sensor; and calculating a thickness of the pipe by deriving a relationship between a frequency and a vibration strength, based on a frequency of the oscillatory waves inputted by the oscillator into the pipe and an amplitude of the oscillatory waves at this frequency detected by the optical fiber sensor.

Due to this structure, the thickness of the pipe can be measured and mapped over a wider area, whereby the malfunction of the pipe can be accurately detected.

The present invention is an apparatus for diagnosing deterioration of a pipe, comprising: the aforementioned multi-point active sensor; a waveform analysis unit connected to the respective active sensors, the waveform analysis unit calculating a thickness of a pipe by deriving a relationship between a frequency and a vibration strength, based on a frequency of oscillatory waves inputted by the oscillator of this active sensor into the pipe and an amplitude of the oscillatory waves at this frequency detected by the optical fiber sensor of this active sensor; a diagnostic database storing judgment threshold values relating to the deterioration of the pipe; and a diagnostic unit connected to the waveform analysis unit and the diagnostic database, the diagnostic unit comparing the thickness of the pipe calculated by the waveform analysis unit with the judgment threshold values stored in the diagnostic database, so as to diagnose the deterioration and the malfunction of the pipe.

Due to this structure, the deterioration and the malfunction of the pipe can be diagnosed in accordance with a size and a thickness thereof which may differ with the industry and the kind. In addition, it is possible, not only to calculate the thickness of the pipe so as to diagnose the deterioration and the malfunction of the pipe, but also to judge a lifetime of the pipe.

The present invention is a method for diagnosing deterioration of a pipe using the aforementioned multi-point active sensor, the method comprising the steps of: passively detecting oscillatory waves generated in a pipe by the optical fiber sensor of at least one active sensor; and analyzing the oscillatory waves generated in the pipe and detected by the optical fiber sensor, so as to detect deterioration and malfunction of the pipe.

Due to this structure, the deterioration and the malfunction of the pipe can be detected, without inputting oscillatory waves into the pipe by the oscillator of the active sensor.

According to the present invention, by using an active sensor including an oscillator capable of inputting oscillatory waves into a pipe and scanning a frequency of the oscillatory waves within a desired range, and an optical fiber sensor mounted on the pipe, the optical fiber sensor detecting the oscillatory waves generated in the pipe, the pipe can be inspected over a wide area thereof for a short period of time at a low manufacturing cost, while a plant is running.

BEST MODE FOR CARRYING OUT THE INVENTION

First Embodiment

A first embodiment of an active sensor according to the present invention is described below, with reference to the drawings. FIGS. 1 to 8, FIGS. 13(a) and 13(b), and FIG. 14 are views showing the first embodiment of the present invention.

Figure 1:
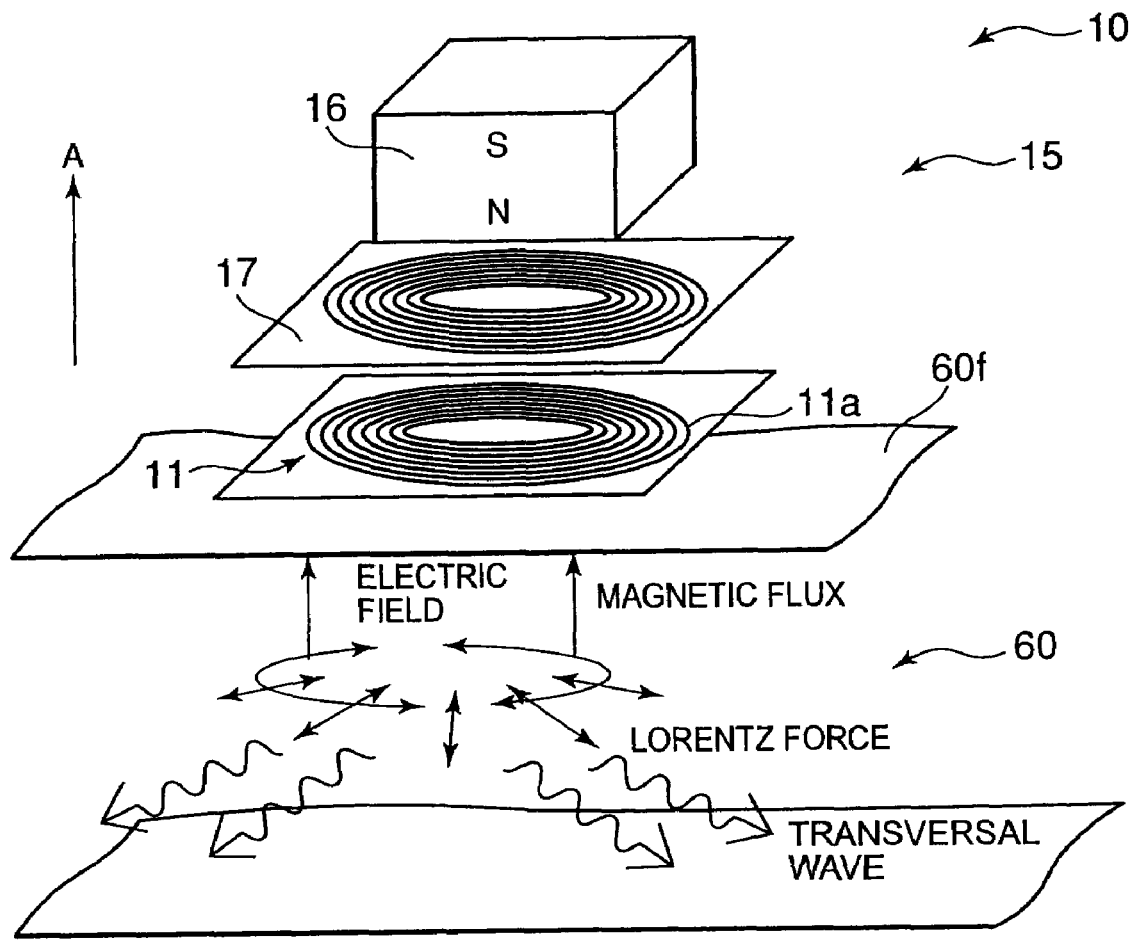
FIG. 1 is a perspective view showing an active sensor in a first embodiment of the present invention.
Figure 2:
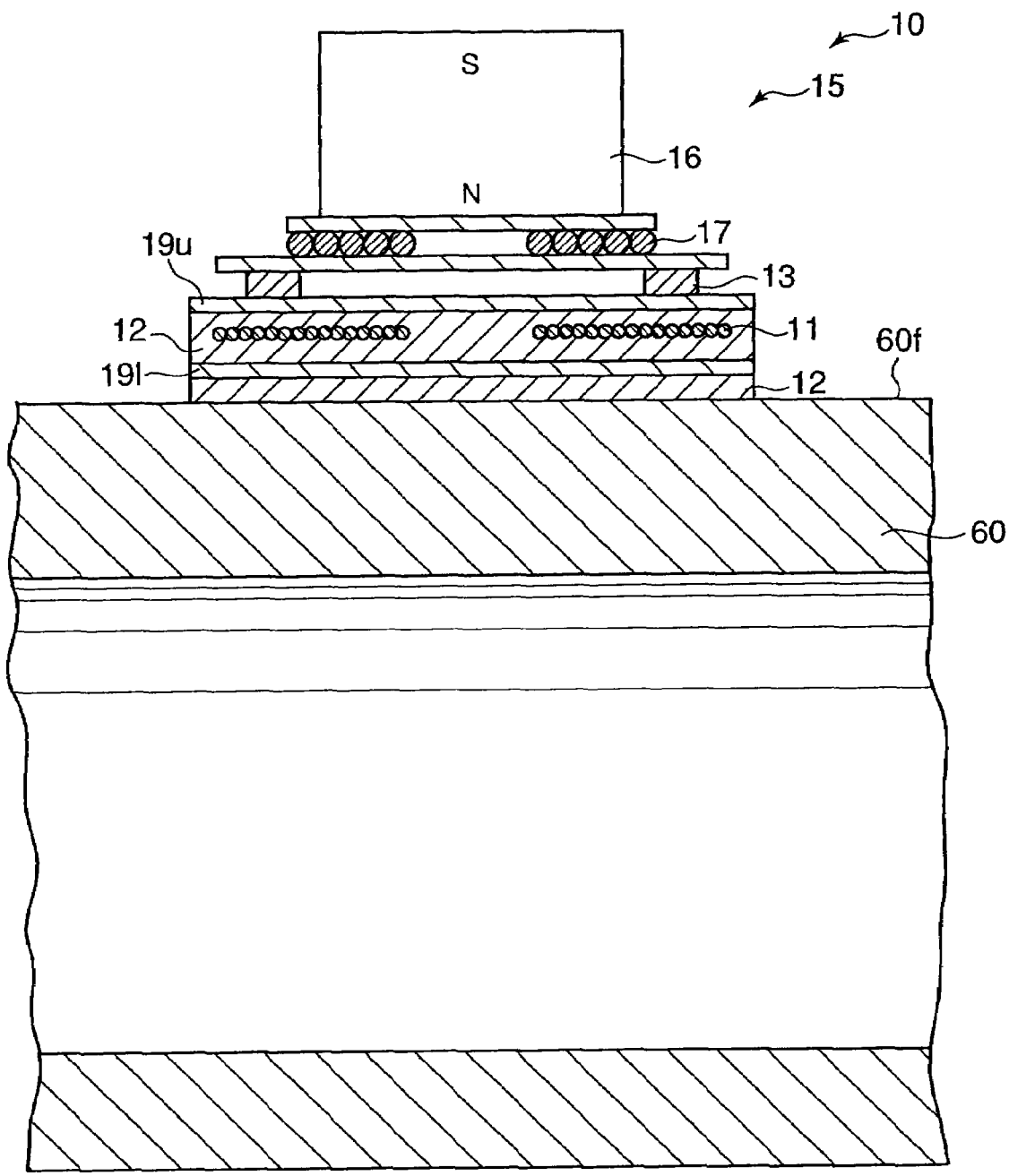
FIG. 2 is a sectional view showing the active sensor in the first embodiment of the present invention.

As shown in FIGS. 1 and 2, an active sensor 10 is positioned on an outside of a pipe 60, and is used for detecting a thickness of the pipe 60. The active sensor 10 has: an oscillator 15 capable of inputting oscillatory waves (ultrasonic waves) into the pipe 60 and scanning frequencies of the oscillatory waves within a desired range; and an optical fiber sensor 11 mounted on the oscillator 15 on a side of the pipe 60, the optical fiber sensor detecting the oscillatory waves generated in the pipe 60.

As shown in FIG. 2, the optical fiber sensor 11 is embedded in a high-temperature adhesive 12 filling a space between a pair of polyimide sheets 19u and 19l. The polyimide sheet 19l, which is located on a lower part of FIG. 2, is attached to the pipe 60 with the high-temperature adhesive 12. Between the upper polyimide sheet 19u and the oscillator 15, there is disposed a holding member 13 that prevents a connection between an oscillation caused by the oscillator 15 and an oscillation propagating in the pipe 60 to be tested. In place of attaching the polyimide sheet 19l to the pipe 60 with the high-temperature adhesive 12, the polyimide sheet 19l may be disposed on the pipe 60 by spraying.

It is preferable to optimize a size of the optical fiber sensor 11 in accordance with a plate thickness value of the pipe 60 to be measured and an oscillatory wavelength, considering an attenuation of ultrasonic waves propagating in the pipe 60. Specifically, an inner diameter of the optical fiber sensor 11 is preferably not less than 5 mm which is a minimum size capable of avoiding a breaking of the optical fiber sensor 11 by bending. Meanwhile, it is desirable to optimize an outer diameter of the optical fiber sensor 11 based on a wavelength of the oscillatory waves propagating inside the pipe 60. The outer diameter is preferably not more than a value that is obtained by adding, to the inner diameter, one half of the wavelength of the oscillatory waves propagating inside the pipe 60. The standard number of winding turns of the optical fiber sensor 11 is 50.

Figure 13:
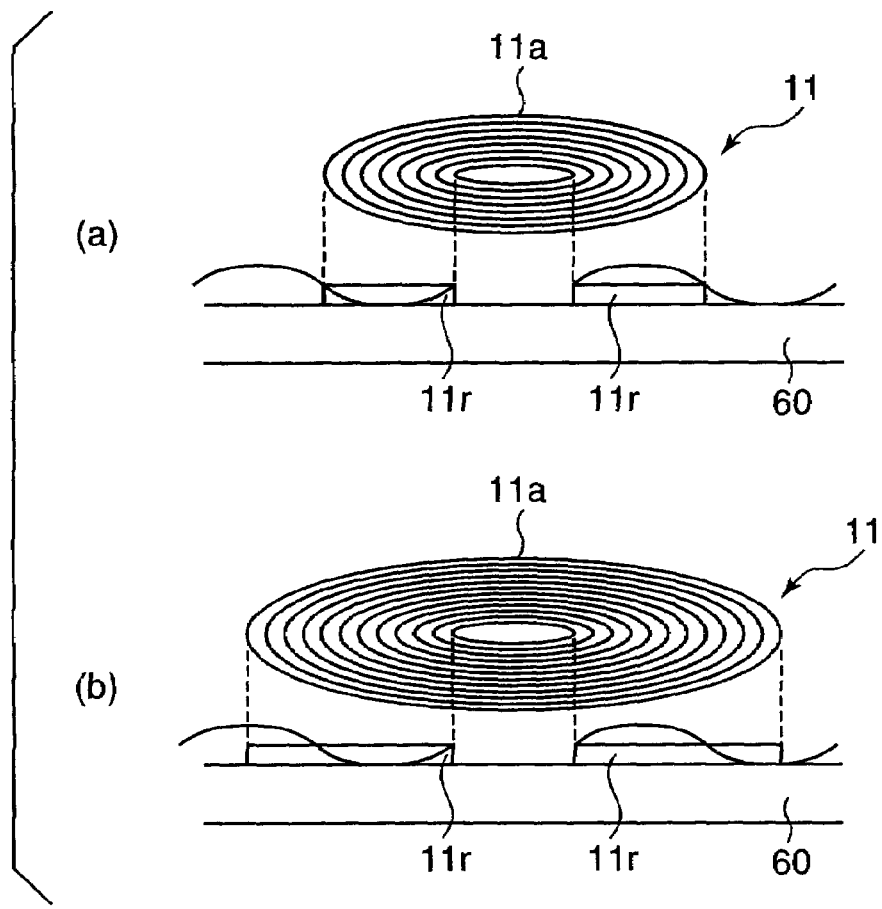
FIG. 13 is a sectional view showing a state in which an optical fiber sensor is connected to a pipe.

FIGS. 13(a) and 13(b) respectively show a state in which the optical fiber sensor 11 is connected to the pipe 60. In FIGS. 13(a) and 13(b), illustration of the oscillator 16 is omitted and is not shown. The wave lines in FIGS. 13(a) and 13(b) show shapes of oscillatory waves propagating inside the pipe 60.

As shown in FIG. 13(a), in a case where the outer diameter of the optical fiber sensor 11 is not more than a value that is obtained by adding, to the inner diameter, one half of the wavelength of the oscillatory waves propagating inside the pipe 60, since amplitudes of the oscillatory waves propagating in aligned sensing part 11a (described below) of the circular or elliptic optical fiber sensor 11 are oriented in the same direction, a large vibration strength can be provided. On the other hand, as shown in FIG. 13(b), in a case where the outer diameter of the optical fiber sensor 11 is larger than a value that is obtained by adding, to the inner diameter, one half of the wavelength of the oscillatory waves propagating inside the pipe 60, the amplitudes of the oscillatory waves propagating in the sensing part 11a undergo vibrations of opposite direction. Namely, since the vibration directions are balanced out by the opposite amplitudes, the vibration strength is lowered. In FIGS. 13(a) and 13(b), the reference number 11r represents a region in which the optical fiber sensor 11 is positioned, i.e., a region between the inner diameter and the outer diameter of the optical fiber sensor 11.

Figure 14:
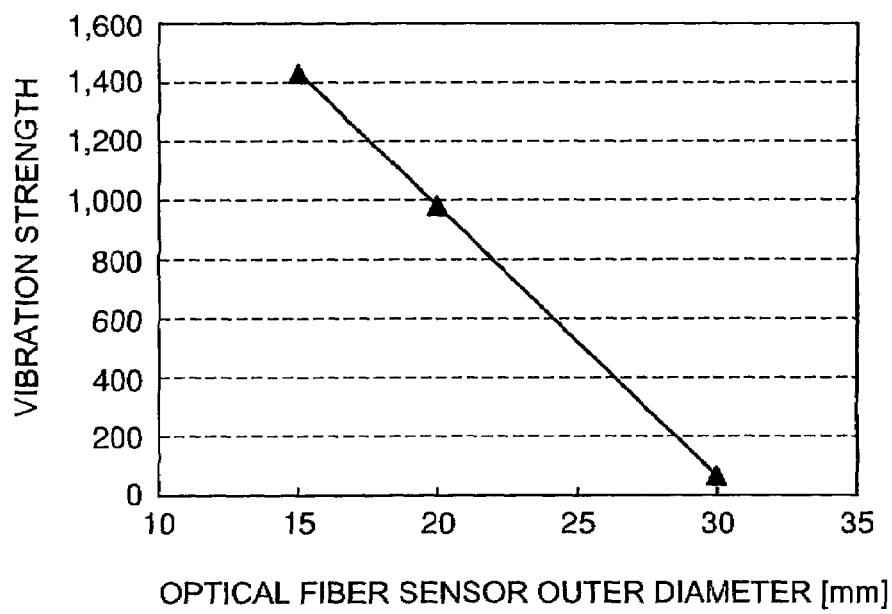
FIG. 14 is a graph showing a relationship between an outer diameter of an optical fiber sensor and a vibration strength.

FIG. 14 is a graph showing a relationship between the outer diameter of the optical fiber sensor 11 (referred to as "optical fiber sensor outer diameter" in FIG. 14) and the vibration strength. Herein, a thickness of a test piece is 5 mm, a wavelength of oscillatory waves propagating in the test piece is 10.7 mm (sonic velocity: 5800 m/sec), and an inner diameter of the optical fiber sensor 11 is 10 mm. In a case where the outer diameter of the optical fiber sensor 11 is 15 mm, which is a value obtained by adding, to the inner diameter (10 mm) of the optical fiber sensor 11, 5 mm which is about one half of the wavelength of the oscillatory waves, it can be seen that the sufficient vibration strength is obtained. On the other hand, in a case where the outer diameter of the optical fiber sensor 11 is a value obtained by adding, to the inner diameter of the optical fiber sensor 11, a value larger than one half of the oscillatory wavelength (in a case where the outer diameter of the optical fiber sensor 11 is larger than 15 mm), it can be seen that the vibration strength is reduced.

The above oscillator 15 is formed from an electromagnet oscillator. To be specific, as shown in FIGS. 1 and 2, the oscillator 15 has a permanent magnet 16 positioned so as to generate a magnetic flux in a normal line direction of a pipe surface 60f (in the A direction shown by the arrow in FIG. 1), and an electric coil 17 disposed on the permanent magnet 16 on a side of the optical fiber sensor 11. In place of disposing the electric coil 17 on the permanent magnet 16 on the side of the optical fiber sensor 11, the electric coil 17 may be wound around the permanent magnet 16. In addition, instead of electric coil 17, there may be used a conductive layer of an optical fiber sensor which is coated with a conductive material such as a metal.

The optical fiber sensor 11 is formed from a fiber-optic Doppler (FOD) sensor (see, FIGS. 3(a) to 3(d) that detects a kinetic strain of the pipe 60, which is generated by the oscillatory waves inputted from the oscillator 15 into the pipe 60. With the use of such an optical fiber sensor 11, strains and vibrations can be detected as the Doppler effect of light based on the FOD principle.

Figure 3:
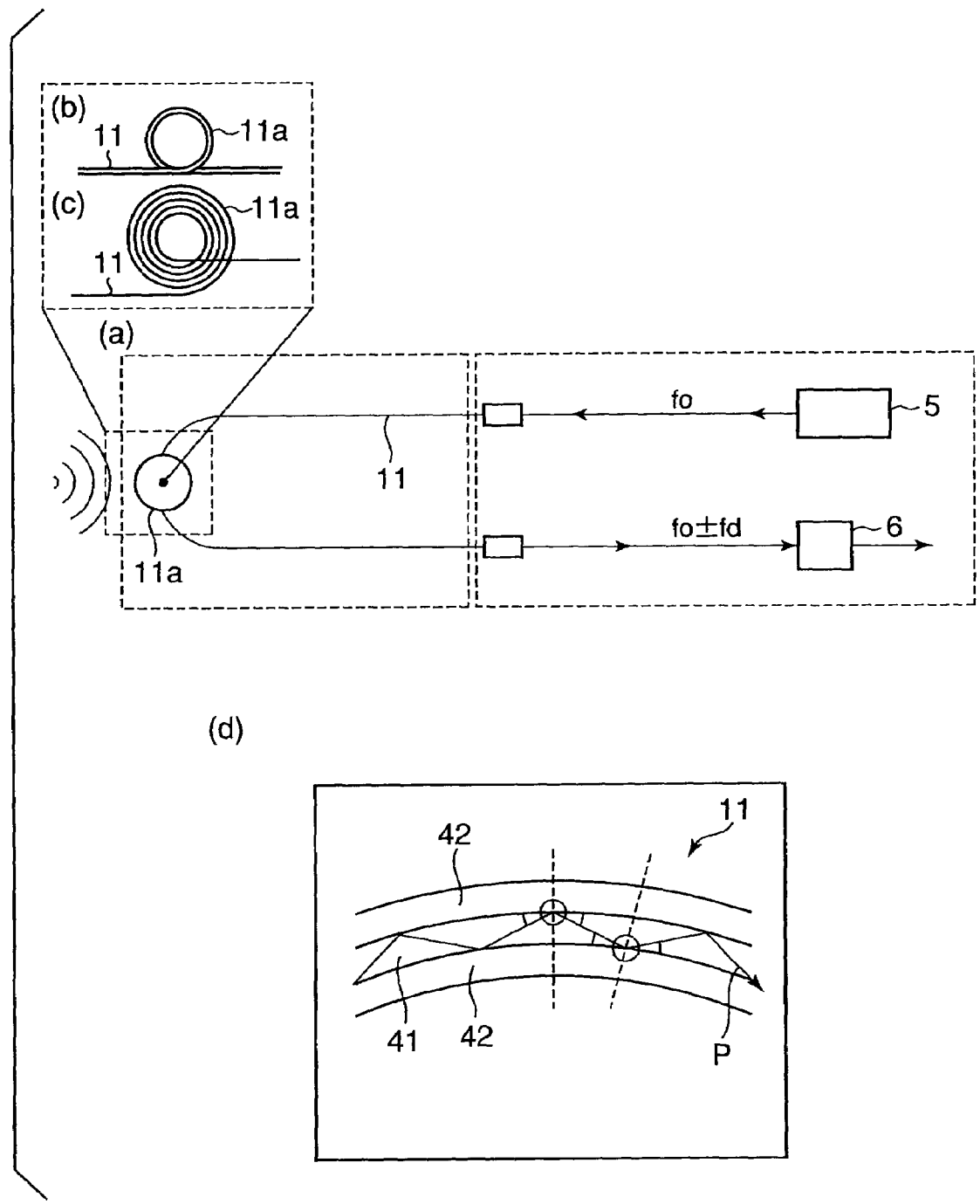
FIG. 3 is a structural view showing an optical fiber sensor in the first embodiment of the present invention.
Figure 4:
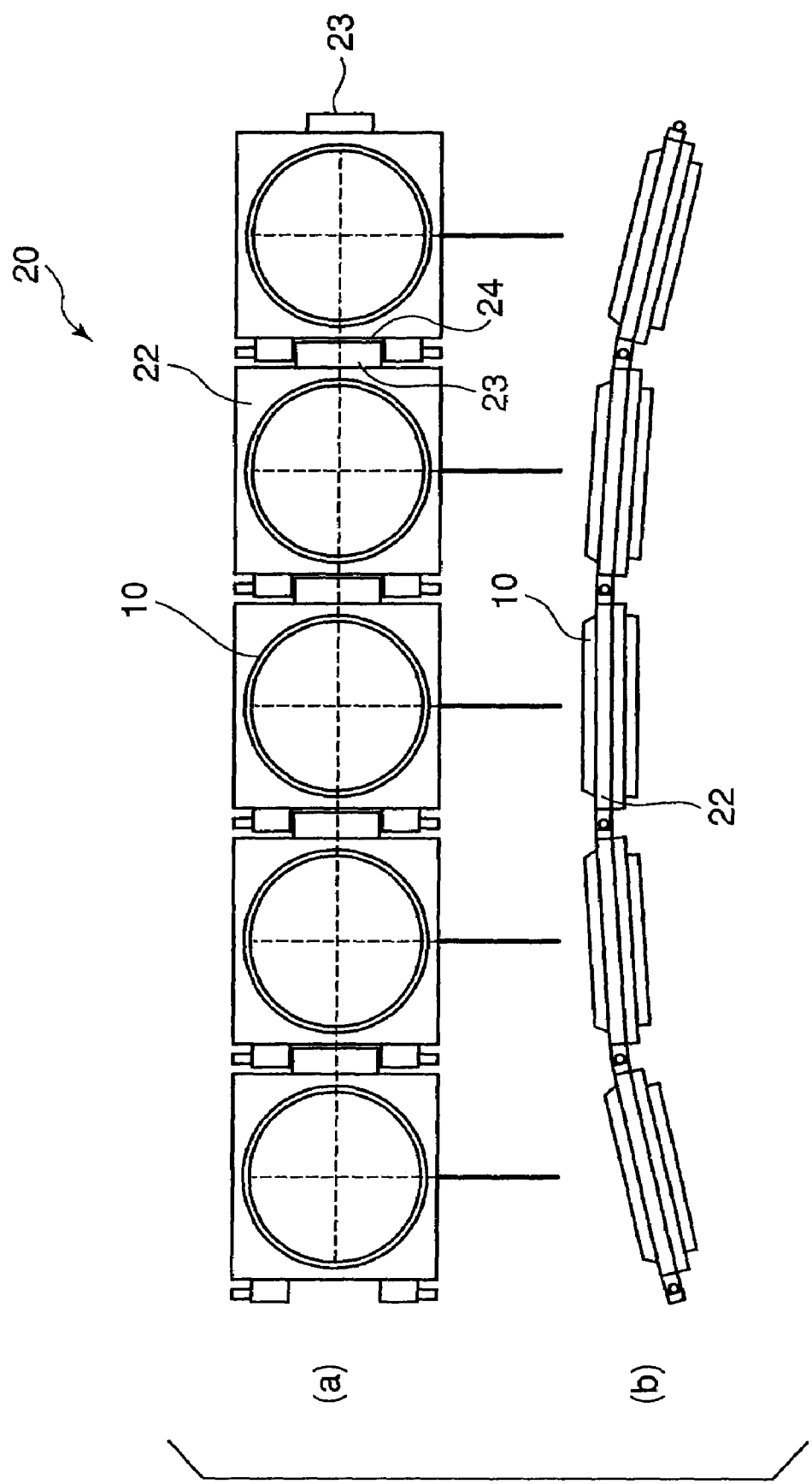
FIGS. 4(a) and 4(b) are a plan view and a side view showing a multi-point active sensor in the first embodiment of the present invention.

As shown in FIGS. 1 and 3, the optical fiber sensor 11 has the circularly winding sensing part 11a. As shown in FIGS. 1 and 2, the oscillator 15 is located at a center of the sensing part 11a.

The sensing part 11a of the optical fiber sensor 11 are subjected to a heat-resistant process, such as a heat-resistant coating using gold, nickel, silica, and polyimide, and/or a narrow tube. Thus, the active sensor 10 can be mounted on even a position where a temperature thereof is raised to a high temperature (between about 350° C. and 750° C.).

As shown in FIG. 3(d), the optical fiber sensor 11 has a core 41 formed from a quartz line or the like, and a clad 42 made of quartz and covering the core 41. As shown in FIG. 3(a), connected to one end of the optical fiber sensor 11 is a light source 5 that supplies a light beam of a predetermined wavelength, such as a laser beam, into the optical fiber sensor 11. Connected to the other end of the optical fiber sensor 11 is a photodetector 6 that detects a deviation of the wavelength which is caused by the kinetic strain in the pipe by the Doppler effect when the light beam has passed through the optical fiber sensor 11.

As described above, since the optical fiber sensor 11 is formed from a fiber-optic Doppler (FOD) sensor, the optical fiber sensor 11 is strained in accordance with strain rates ($\epsilon x$; strain rate in an x direction, $\epsilon y$; strain rate in a y direction) generated in the pipe 60, so that a light beam P incident on the optical fiber sensor 11 from the light source 5 at a frequency f0 repeatedly reflects in the core 41 of the sensing part 11a of the optical fiber sensor 11 so as to produce the Doppler effect (see, FIG. 3(d)), and emerges at a frequency f0±fd to the photodetector 6 (see, FIG. 3(a)).

FIG. 3(b) is a partial enlarged view of the sensing part 11a of the optical fiber sensor 11. FIG. 3(c) is a further enlarged view of FIG. 3(b). FIG. 3(d) is a view showing a state in which the light beam P repeatedly reflects in the core 41 of the sensing part 11a of the optical fiber sensor 11.

The deviation of the frequency fd is concretely represented as the following (Expression 1).

$$f_d = n_{eq} N \pi R_{av} (\dot{\epsilon}_x + \dot{\epsilon}_y)/\lambda_0 \quad \text{(Expression 1)}$$

in which:

$n_{eq}$; transmission refractive index in fiber

N; winding number $R_{av}$; average winding diameter $\lambda_0$; wavelength of incident light beam As shown in FIGS. 4(a) and 4(b), by linearly (serially) arranging the plurality of active sensors 10, a multi-point active sensor 20 can be obtained. The respective active sensors 10 are connected to each other by connection members 22 having a plasticity and a flexibility. FIG. 4(a) is a plan view showing the multi-point active sensor 20 from above, and FIG. 4(b) is a side view showing the multi-point active sensor 20 from the lateral side.

To be specific, as shown in FIG. 4(a), each of the active sensors 10 is located in the connection member 22 having a projection 23 and a recess 24. The projection 22 of each connection member 22 is fitted in the recess 24 of the adjacent connection member 22, whereby each of the connection members 22 is connected to the connection members 22 adjacent thereto.

Figure 5:
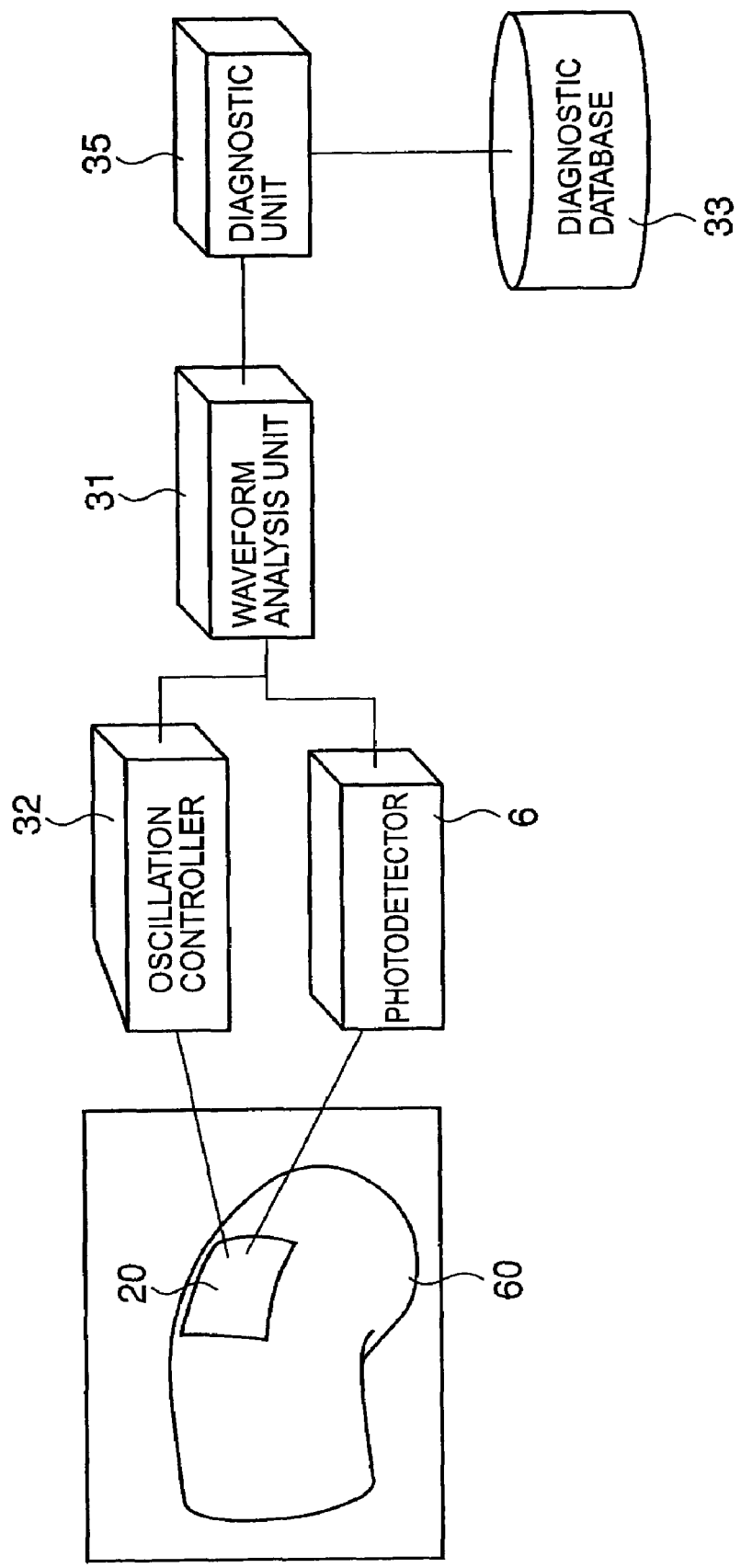
FIG. 5 is a structural view showing an apparatus for diagnosing deterioration of a pipe in the first embodiment of the present invention.

In FIG. 5 (see, also FIG. 1), connected to each electric coil 17 of the oscillator 15 of the active sensor 10 of the multi-active sensor 20 is an oscillation controller 32 that supplies an alternating current to the electric coil 17. The oscillation controller 32 is provided with a function generator (not shown) capable of scanning a frequency of the alternating current supplied by the oscillation controller 32. In addition, the oscillation controller 32 is capable of adjusting an intensity of the current to be supplied.

As shown in FIG. 5, an apparatus for diagnosing deterioration of a pipe is composed of: the above multi-point active sensor 20; a waveform analysis unit 31 connected to the oscillation controller 32 and the photodetector 6, the waveform analysis unit 31 calculating a thickness of the pipe 60; a diagnostic database 33 storing judgment threshold values relating to the deterioration of the pipe 60; and a diagnostic unit 35 connected to the waveform analysis unit 31 and the diagnostic database 33, the diagnostic unit 35 comparing the thickness of the pipe 60 calculated by the waveform analysis unit 31 with the judgment threshold values stored in the diagnostic database 33 so as to diagnose the deterioration of the pipe 60.

Herein, the waveform analysis unit 31 calculates the thickness of the pipe 60 by deriving a relationship between a frequency and a vibration strength, based on a frequency of the oscillatory waves inputted into the pipe 60 by the oscillator 15 of the active sensor 10 in the multi-point active sensor 20 and an effective value of an amplitude of the oscillatory waves or a frequency spectral intensity obtained by Fourier converting the oscillatory waves at the frequency detected by the optical fiber sensor 11 of the active sensor 10.

Connected to each of the oscillators 15 is a switching mechanism (not shown) which can be selectively switched on and off from a remote position. Thus, it is possible to select the active sensor(s) 10 to be activated in the multi-point active sensor 20. Accordingly, which point(s) of the pipe 60 to be measured can be freely selected.

Next, an effect of this embodiment as structured above is described.

At first, a relationship between a frequency of oscillatory waves inputted into the pipe 60 by the oscillator 15 of the active sensor 10 and the thickness of the pipe 60 is described.

Figure 6:
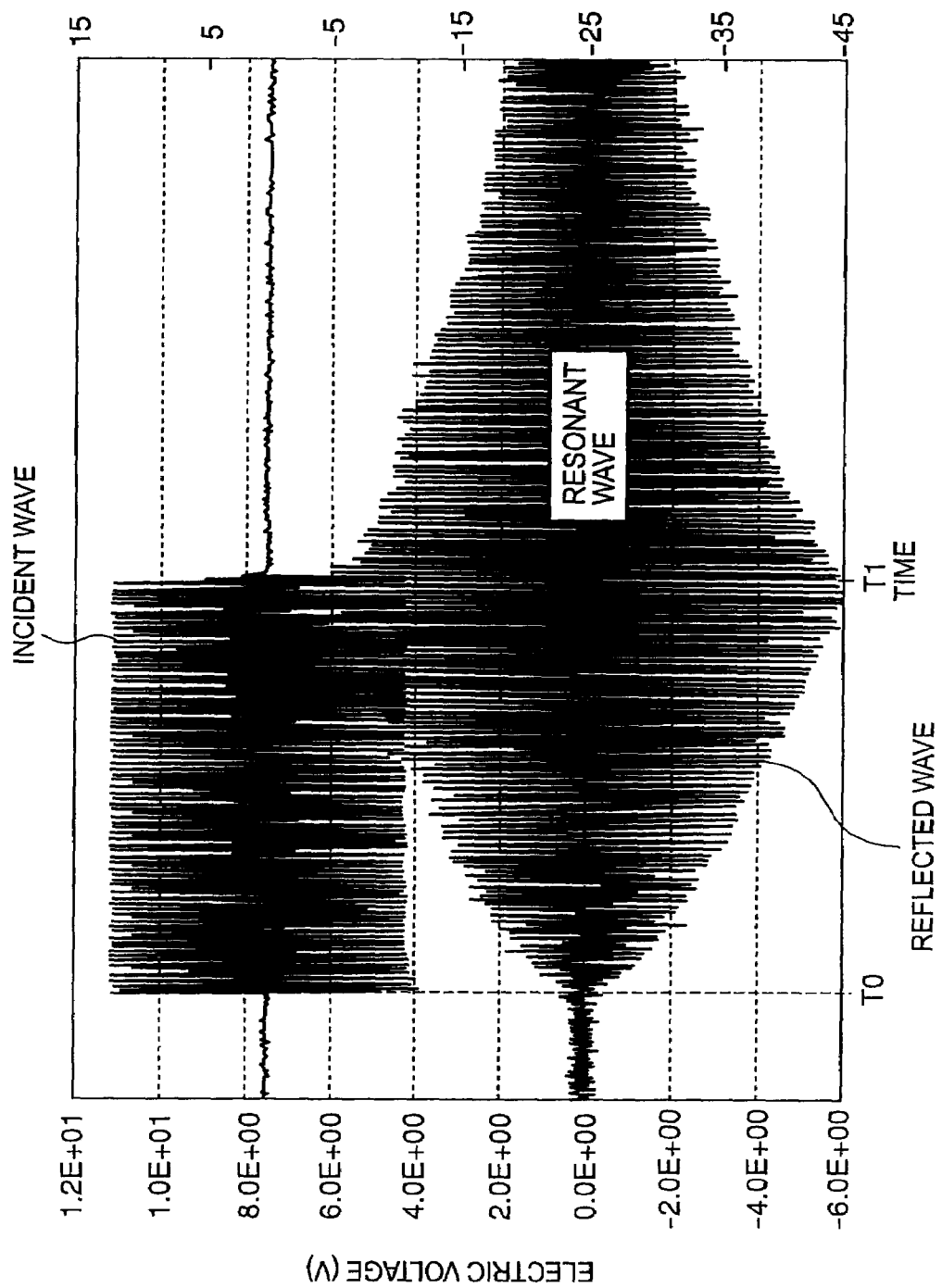
FIG. 6 is a graph showing incident waves, reflected waves, and resonant waves, which are observed by the apparatus for diagnosing deterioration of a pipe in the first embodiment of the present invention.

As shown in FIG. 6, when a relationship of "λ=2L" is satisfied between the thickness L of the pipe 60 and the wavelength λ of the oscillatory waves inputted into the pipe 60, the oscillatory waves (incident waves) inputted into the pipe 60 and the oscillatory waves (reflected waves) detected by the optical fiber sensor 11 sympathetically vibrate so that resonant waves are observed. The resonant waves herein mean reflected waves which are observed after the incident waves are stopped (after a time point T1 in FIG. 6). The reference character T0 shows a time point at which the incident waves are started to be inputted, and T1 shows a time point at which the incident operation is stopped.

Thus, the thickness L of the pipe 60 can be measured by a reverse operation from the wavelength λ. Namely, when the following condition is satisfied, the ultrasonic wave resonates.

2d=λ Expression (2) in which a thickness of a metal plate is d and a wavelength of an ultrasonic wave is λ.

This can be rewritten with a frequency f of the ultrasonic wave to obtain the following Expression (3). Thus, when a resonant frequency and a sonic velocity can be grasped, the plate thickness can be reversely operated.

$$f = \frac{v}{2} \cdot d^{-1} (v\text{: sonic velocity} = 5900 \text{ m/sec})$$ Expression (3)

For example, in a case where the pipe 60 formed from a steel plate having a thickness of 15 mm is measured, when ultrasonic waves at a frequency of 200 kHz are inputted, the resonance occur.

After the optical fiber sensor 11 whose winding number is 50 is attached with an instant adhesive to surfaces of SUS 304 (stainless steel) plates having the same diameter of 200 mm, and thicknesses of 5 mm, 7 mm, 10 mm, 15 mm, 20 mm, 25 mm, and 30 mm, sine waves amplified to 150 Vp-p by an amplifier at every 1 kHz in increment in a range from 50 kHz to 500 kHz are generated. Then, resonant waves corresponding to each frequency can be detected (FIG. 6).

Figure 7:
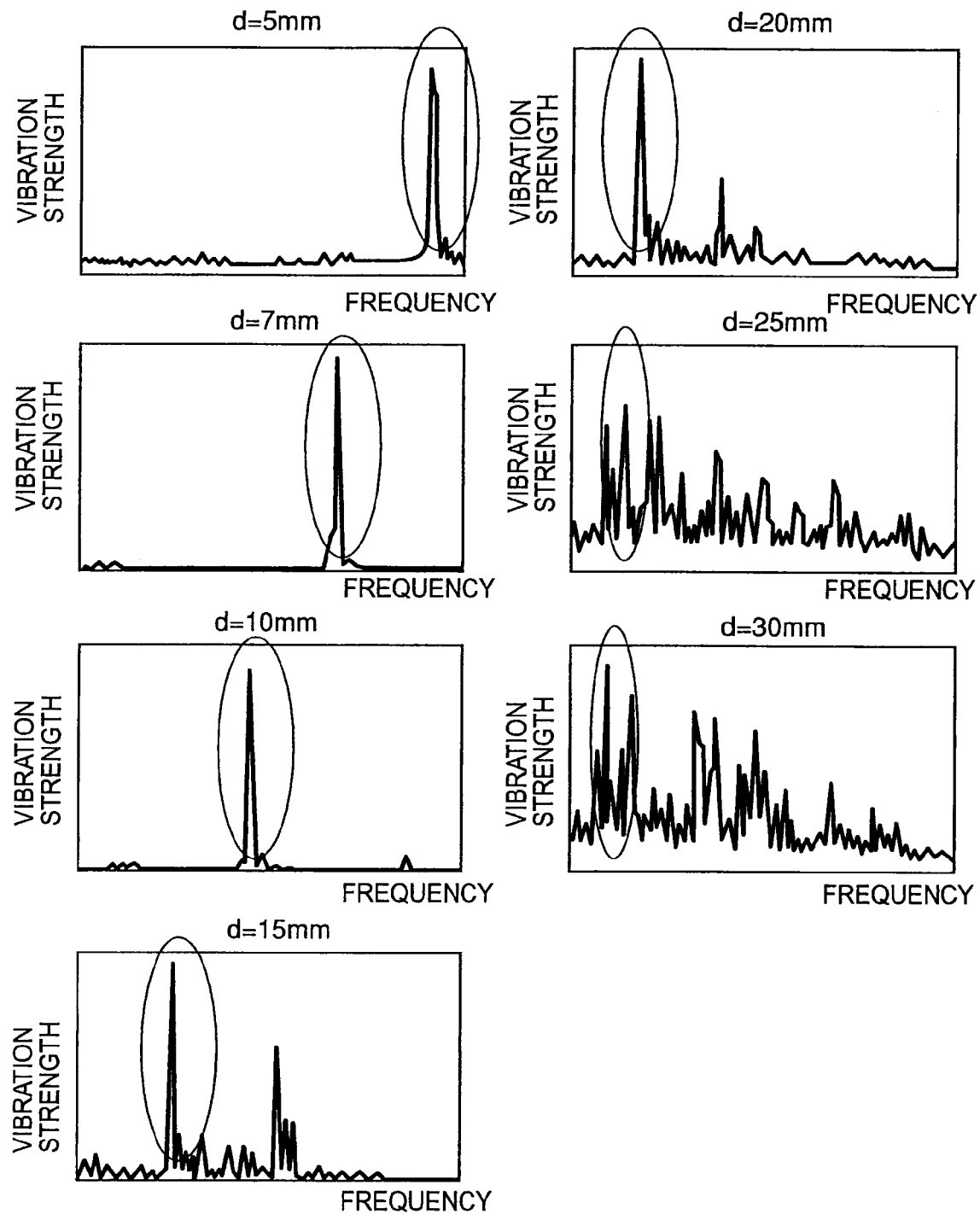
FIG. 7 is a graph showing relationship between a frequency and a vibration strength, which is obtained by the apparatus for diagnosing deterioration of a pipe in the first embodiment of the present invention.
Figure 8:
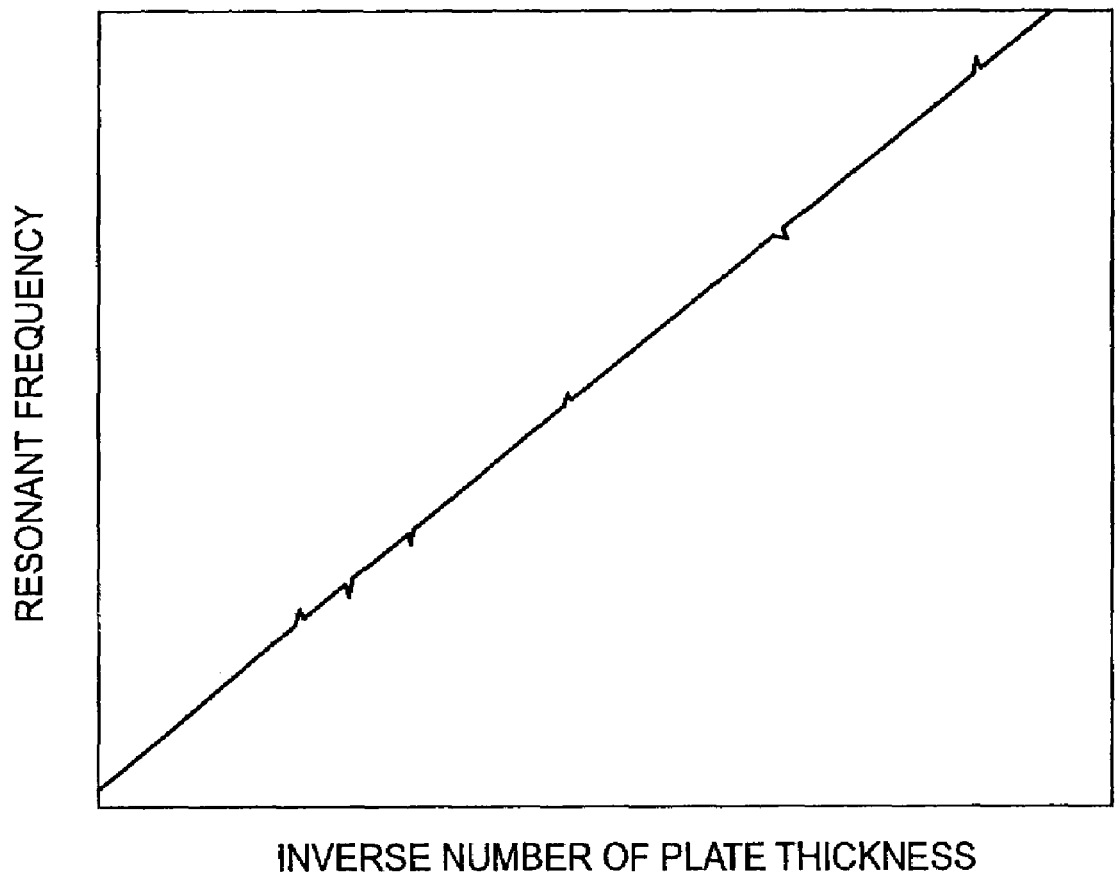
FIG. 8 is a graph showing a relationship between an inverse number of a plate thickness and a resonant frequency, which is obtained by the apparatus for diagnosing deterioration of a pipe in the first embodiment.

Then, when a value obtained by integrating an intensity (voltage value) of the resonant waves in a preset time period relative to the time is defined as "vibration strength", vibration strengths at the respective frequencies can be derived (see, FIG. 6). From the vibration strengths at the respective frequency as obtained above, a relationship between the frequency and the vibration strength can be derived, which is shown in FIG. 7. From the frequency when the vibration strength is highest (frequency corresponding to the region surrounded by the elliptic circle), the resonant frequency can be derived. FIG. 8 shows a relationship between a resonant frequency and an inverse number of the plate thickness of SUS 304. It can be understood from FIG. 8 that the relationship defined by the Expression (3) is satisfied between the resonant frequency and the inverse number of the plate thickness of SUS304.

Next, a method of diagnosing deterioration and malfunction of the pipe 60 is described.

At first, oscillatory waves are inputted into the pipe 60 by the oscillators 15 of the active sensors 10 of the multi-point active sensor 20. Specifically, by supplying an alternating current to the electric coil 17 of the oscillator 15 by the oscillation controller 32, the Lorentz force is applied to the permanent magnet 16, to thereby input transversal waves to the pipe 60 in a thickness direction thereof (see, FIGS. 1 and 5).

A frequency of the alternating current is changed by using the function generator of the oscillation controller 32, and the alternating current is scanned with a desired frequency bandwidth. By connecting an amplifier to the function generator, it is possible to optionally change both a frequency and an intensity of the input waves.

On the occasion of construction or periodic inspection of the pipe 60, such a multi-point active sensor 20 is preferably mounted on an elbow portion and an orifice downstream portion of the pipe 60, which are susceptible to erosion and corrosion.

Then, the oscillatory waves generated in the pipe 60 are detected, and are sent to the photodetector 6 by the optical fiber sensor 11 of the active sensor 10 (see, FIG. 5). Since the oscillator 15 is positioned at the center of the sensing part 11a, the oscillatory waves generated in the pipe 60 can be detected with an improved sensitivity (see, FIGS. 1 and 2). In addition, since the optical fiber sensor 11 is formed from a fiber-optic Doppler sensor, the waves can be detected with an excellent sensitivity over a wide frequency bandwidth ranging from 0 Hz (excluding zero) and several MHz.

Then, based on a frequency of the oscillatory waves inputted into the pipe 60 by the oscillator 15 of the active sensor 10, and an amplitude of the oscillatory waves at this frequency detected by the optical fiber sensor 11 of this active sensor 10, a relationship between the frequency and the vibration strength is derived by the waveform analysis unit 31 connected to the oscillation controller 32 and the photodetector 6 (see, FIG. 7). Thereafter, the waveform analysis unit 31 derives a resonant frequency based on the relationship between the frequency and the vibration strength, and calculates the thickness of the pipe 60 based on the Expression (3) or the graph shown in FIG. 8.

Then, the thickness of the pipe 60 calculated by the waveform analysis unit 31 and the judgment threshold values stored in the diagnostic database 33 are compared to each other, and the deterioration of the pipe 60 or the malfunction of the pipe 60 is diagnosed.

In this manner, since the deterioration of the pipe 60 is diagnosed with the use of the judgment threshold values stored in the diagnostic database 33, the pipe 60 can be diagnosed in accordance with its size and thickness, which may differ with the industry and the kind. In addition, it is possible, not only to calculate the thickness of the pipe 60 so as to diagnose the deterioration and the malfunction of the pipe 60, but also to judge a lifetime of the pipe 60.

As has been described above, by mounting the multi-point active sensor 20 on the outside of the pipe 60, it is possible to, while a plant is running, calculate the thickness of the pipe 60 so as to diagnose the deterioration and the malfunction of the pipe 60 over a wide area, for a short period of time, without detaching an heat-insulation material from the pipe 60. Thus, the time and the number of steps required for the inspection can be significantly reduced. Accordingly, the time for the periodic inspection can be reduced, and the corrective maintenance service can be improved.

As shown in FIGS. 4(a) and 4(b), the respective active sensors 10 included in the multi-point active sensor 20 are connected to each other by the connection members 22 having a plasticity and a flexibility. Thus, the multi-point active sensor 20 can be mounted on a curved portion and an elbow portion of the pipe 60, whereby portions of the pipe 60 where a thickness thereof is prone to be reduced can be inspected.

Since the active sensor 10 in this embodiment can be manufactured from the electric coil 17, the permanent magnet 16, and the optical fiber sensor 11, a manufacturing cost for the active sensor 10 is considerably inexpensive.

The reliability of the multi-point active sensor 20 can be prolonged, by reducing the size of the oscillator 15 of the active sensor 10 so as to restrain a sensing area, by optimizing a distance between the active sensors 10, by enhancing a connection between the active sensors 10, by enhancing a decomposability when measuring a thickness, by improving a heat-resistant property of the adhesive 12, and by improving an absorbance of the active sensor 10 at an elbow portion of the pipe 60.

Further, the use of the smaller oscillator 15, which can be driven at a low voltage, and the optical fiber sensor 11, which can detect a wave with a short FOD gauge length, can enhance practical usefulness.

The precision of measuring the thickness of the pipe 60 is determined by parameters such as a power of the oscillatory waves from the oscillator 15 (capacity of the amplifier connected to the function generator), a magnetic force of the permanent magnet 16, the turning number of the electric coil 17, a sensitivity of the optical fiber sensor 11 itself (the turning number of the optical fiber sensor 11), and a heat resistance.

In the above embodiment, the oscillator 15 formed from an electromagnetic oscillator is described by way of example. However, not limited thereto, there may be used an oscillator 15 formed from a piezoelectric oscillator having a piezoelectric element. When such a piezoelectric oscillator is used, a strong oscillation can be provided at a lower electric power.

Further, in the above embodiment, the optical fiber sensor 11 having the circularly winding sensing part 11a is described by way of example. However, not limited thereto, there may be used an optical fiber sensor 11 having an elliptically winding sensing part. When such an optical fiber sensor 11 having the elliptically winding sensing part is used, the optical fiber sensor 11 can have an anisotropy.

Alternative Example 1

Next, an alternative example 1 of the first embodiment is described with reference to FIGS. 9(a) to 9(c). In the alternative example 1 of the first embodiment shown in FIGS. 9(a) to 9(c), in place of using the multi-point active sensor 20 in which the plurality of active sensors 10 are linearly arranged, there is used a multi-point active sensor 20 in which the plurality of active sensors 10 are arranged in matrix. Other structures of the alternative example 1 are substantially the same as those of the first embodiment shown in FIGS. 1 to 8.

Figure 9:
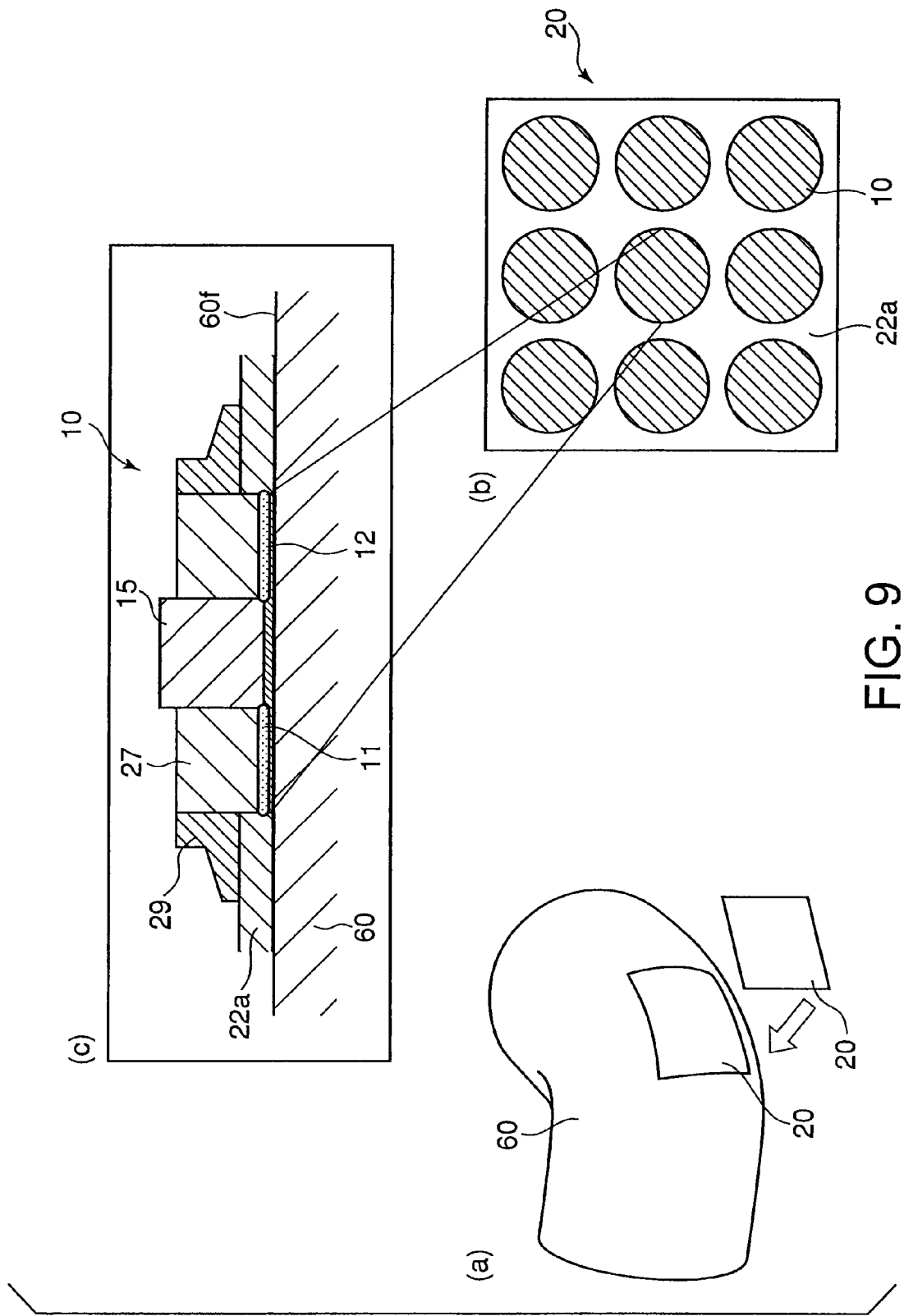
FIG. 9 is a structural view showing a multi-point active sensor and an active sensor in an alternative example 1 in the first embodiment of the present invention.

In the alternative example 1 shown in FIGS. 9(a) to 9(c), the same parts as those in the first embodiment shown in FIGS. 1 to 8 are shown by the same reference numbers, and a detailed description thereof is omitted.

As shown in FIG. 9(b), the multi-point active sensor 20 in this embodiment has the plurality of active sensors 10 arranged in matrix. To be more specific, as shown in FIG. 9(b), in the multi-point active sensor 20, there are arranged, in a square area of 100 mm by 100 mm, the nine active sensors 10 of about 30 mmφ in 3×3 matrix.

As shown in FIG. 9(c), each of the active sensors 10 included in the multi-point active sensor 20 of the alternative example 1 has: an oscillator 15 mounted on a pipe surface 60f of a pipe 60, the oscillator 15 inputting oscillatory waves into the pipe 60, and an optical fiber sensor 11 mounted on an outer surface of the pipe 60 so as to surround the oscillator 15, the optical fiber sensor 11 detecting oscillatory waves generated in the pipe 60. The oscillator 15 and the optical fiber sensor 11 are attached to the outer surface of the pipe 60 with a heat-resistant adhesive 12 (or tackifier).

As shown in FIGS. 9(b) and 9(c), the respective active sensors 10 are connected to each other by a connection member 22a made of a silicon sheet. On the connection member 22a and at an outer periphery of the optical fiber sensor 11, there is disposed a case 29 made of metal or engineering plastic. A space between the oscillator 15 and the case 29 is filled with silicon 27.

By using such a multi-point active sensor 20, a thickness of the pipe 60 can be measured and mapped over a wider area, whereby the deterioration and the malfunction of the pipe 60 can be more precisely detected.

In the alternative example 1, there is described by way of example the active sensor 10 including the oscillator 15 mounted on the outer surface of the pipe 60 and the optical fiber sensor 11 mounted on the outer surface of the pipe 60 so as to surround the oscillator 15. However, not limited thereto, there may be used an active sensor 10 including an oscillator 15, and an optical fiber sensor 11 mounted on the oscillator 15 on a side of the pipe 60, as shown in the first embodiment.

To the contrary, there may be used, as the active sensor in the first embodiment, an active sensor 10 as shown in the alternative example 1 including an oscillator 15 mounted on an outer surface of a pipe 60 and an optical fiber sensor 11 mounted on the outer surface of the pipe 60 so as to surround the oscillator 15.

Alternative Example 2

Next, an alternative example 2 of the first embodiment is described with reference to FIG. 10 and FIGS. 11(a) and 11(b). In the alternative example 2 shown in FIG. 10 and FIGS. 11(a) and 11(b), in place of using the oscillator 15 including the permanent magnet 16 positioned so as to generate a magnetic flux in a normal line direction of the pipe surface 60f (in the A direction shown by the arrow in FIG. 10) and the electric coil 17 disposed on the permanent magnet 16 on a side of the optical fiber sensor 11, there is used an oscillator 15 including a pair of permanent magnets 16 positioned so as to generate a magnetic flux in a direction perpendicular to a normal line direction of the pipe surface 60f (in the A direction shown by the arrow in FIG. 10), and an electric coil 17 disposed between the pair of permanent magnets 16. Other structures of the alternative example 2 are substantially the same as those of the first embodiment shown in FIGS. 1 to 8.

Figure 10:
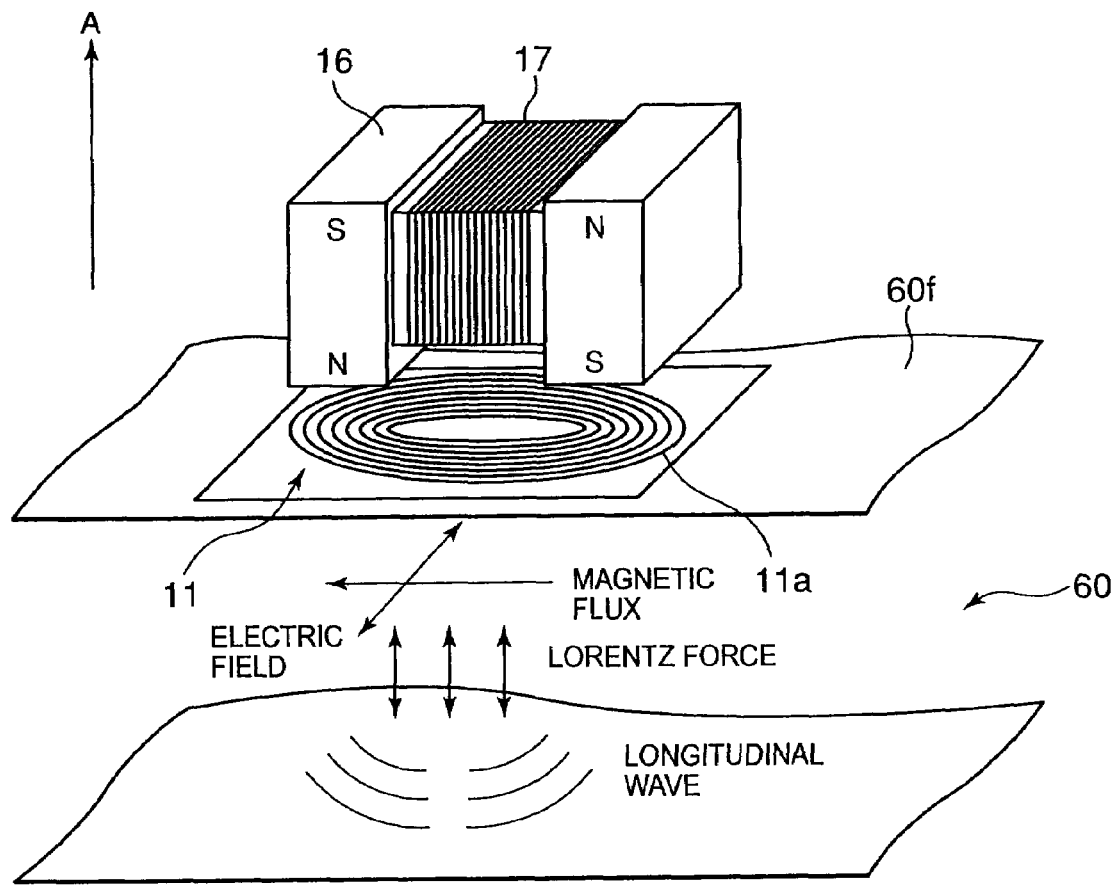
FIG. 10 is a perspective view showing an active sensor in an alternative example 2 in the first embodiment of the present invention.
Figure 11:
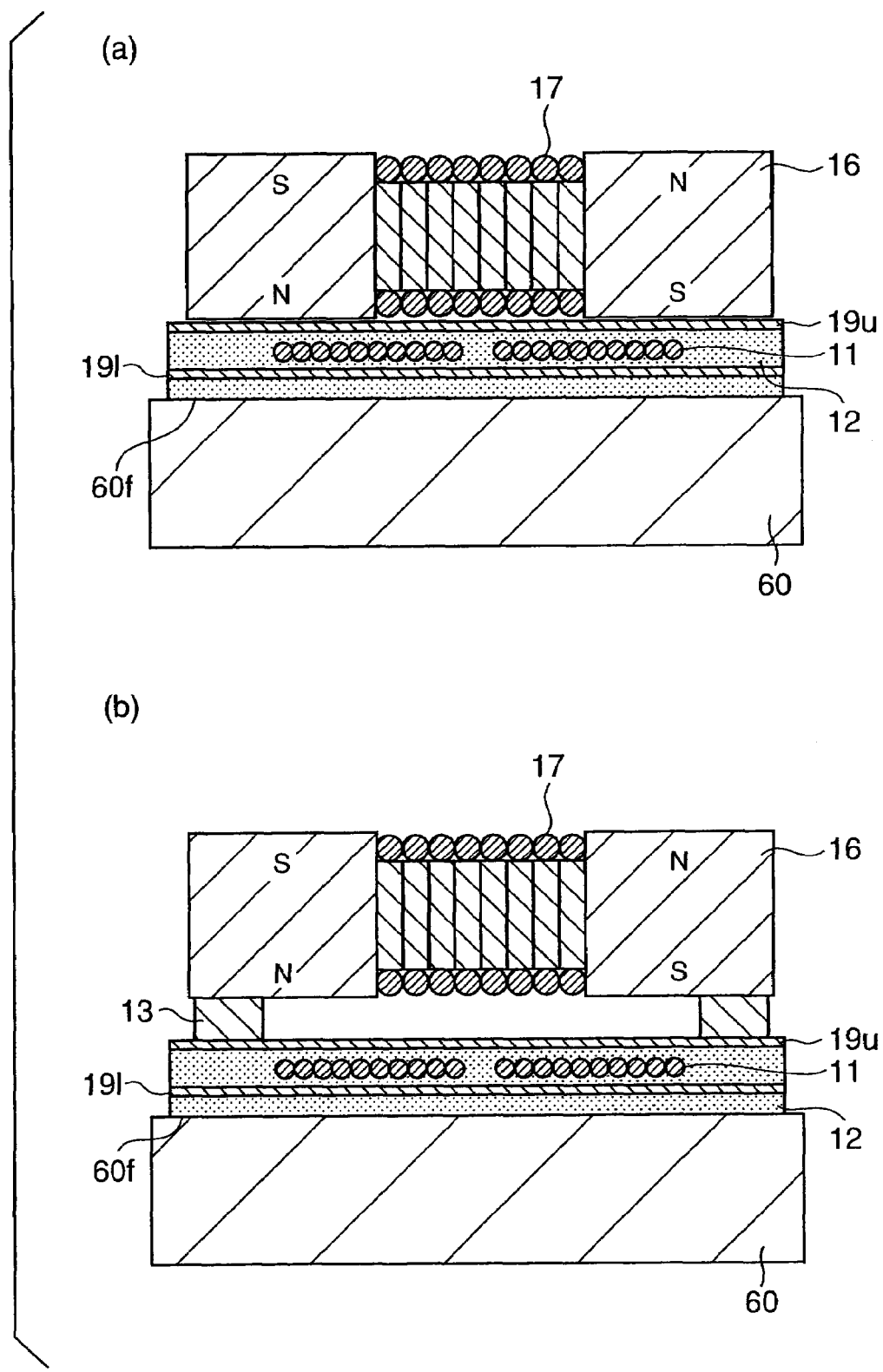
FIG. 11 is a sectional view showing an active sensor in the alternative example 2 in the first embodiment of the present invention.

In the alternative example 2 shown in FIG. 10 and FIGS. 11(a) and 11(b), the same parts as those in the first embodiment shown in FIGS. 1 to 8 are shown by the same reference numbers, and a detailed description thereof is omitted.

As shown in FIG. 10 and FIGS. 11(a) and 11(b), the oscillator 15 in this alternative example has the pair of permanent magnets 16 positioned so as to generate a magnetic flux in a direction perpendicular to a normal line direction of the pipe surface 60f, and the electric coil 17 disposed between the pair of permanent magnets 16. Thus, by supplying an alternating current to the electric coil 17 disposed between the pair of permanent magnets 16 from an oscillation controller 32, the Lorentz force can be applied to the pair of permanent magnets 16 positioned so as to generate a magnetic flux in a direction perpendicular to a normal line direction of the pipe surface 60f, to thereby input longitudinal waves into the pipe 60 in a thickness direction thereof (see, FIGS. 5 and 10).

As shown in FIG. 11(b), a holding member 13 may be provided between the permanent magnets 16 and a polyimide sheet 19u. Alternatively, as shown in FIG. 11(a), the provision of the holding member 13 between the permanent magnets 16 and the polyimide sheet 19u may be omitted.

Second Embodiment

Next, a second embodiment of the present invention is described with reference to FIG. 12. In the second embodiment shown in FIG. 12, a waveform analysis unit 31 has the following three functions, i.e., (1) a frequency analysis function considering a burst behavior at a high frequency area (discrimination from a steady noise), (2) a behavior observation function of standing waves at a low frequency area (discrimination from a steady noise), and (3) a "steady"/"non-steady" observation function utilizing a neutral network and the like. In addition, a diagnostic database 33 stores information relating to deterioration and malfunction of a pipe 60, the information being to be compared to oscillatory waves generated in the pipe 60 for some reason or other which are detected by an optical fiber sensor 11 of an active sensor 10. Other structures of the second embodiment 2 are substantially the same as those of the first embodiment shown in FIGS. 1 to 8.

Figure 12:
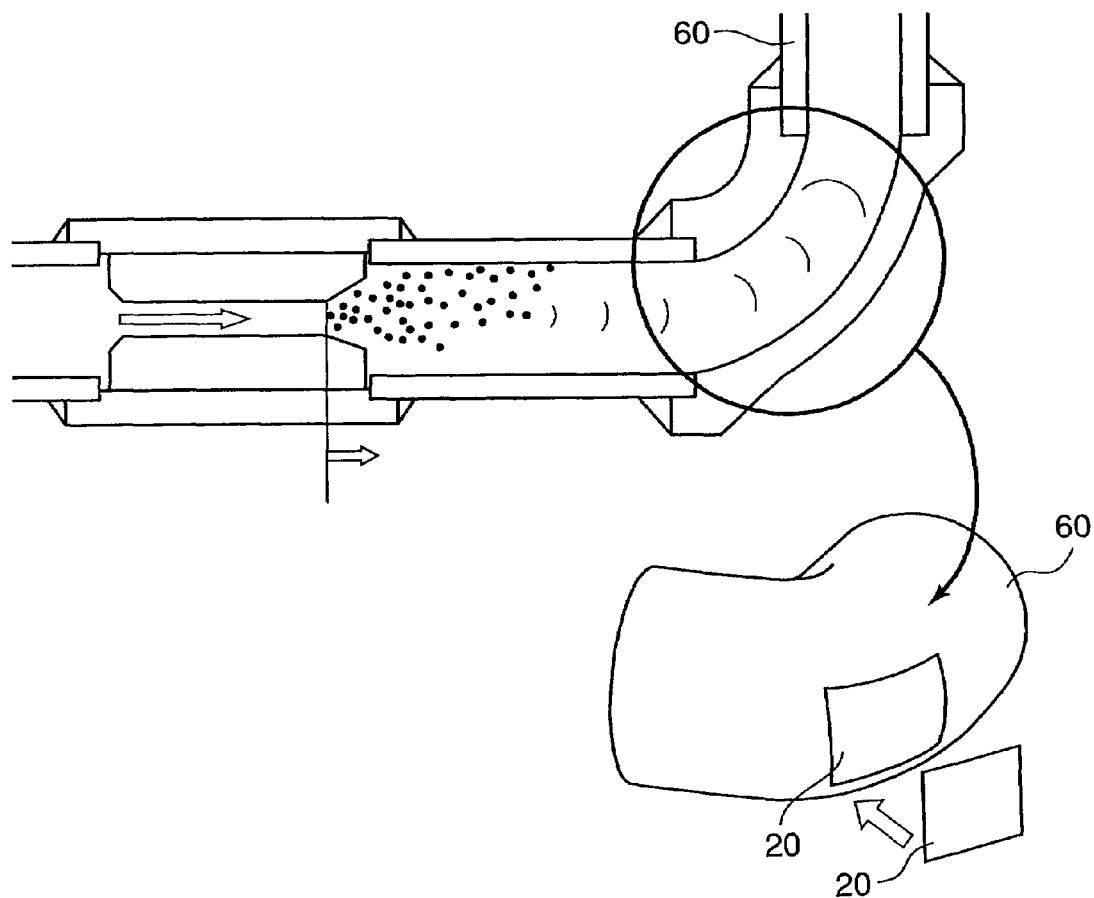
FIG. 12 is a structural view showing a multi-point active sensor in a second embodiment of the present invention.

In the second embodiment shown in FIG. 12, the same parts as those in the first embodiment shown in FIGS. 1 to 8 are shown by the same reference numbers, and a detailed description thereof is omitted.

At first, by the optical fiber sensor 11 of the active sensor 10, oscillatory waves generated in the pipe 60 for some reason or other (for example, oscillatory waves caused by a bust impact, or oscillatory waves generated in an abnormal state which do not appear in a steady state) are passively detected (see, FIG. 12).

Then, due to the (1) a frequency analysis function considering a burst behavior at a high frequency area (discrimination from a steady noise), (2) a behavior observation function of a standing wave at a low frequency area (discrimination from a steady noise), and (3) a "steady"/"non-steady" observation function utilizing a neutral network and the like, of the waveform analysis unit 31, a waveform of the oscillatory waves generated in the pipe 60 or some reason or other is analyzed.

Then, a diagnostic unit 35 analyzes the oscillatory waves detected by the optical fiber sensor 11 of the active sensor 11, referring to the information relating to deterioration and malfunction of the pipe 60, which has been stored in the diagnostic database 33 beforehand, so that the deterioration and the malfunction of the pipe 60 is detected (see, FIG. 5).

As shown in the first embodiment, the diagnostic unit 35 can also detect the thickness of the pipe 60 from a resonant frequency derived from an amplitude of the oscillatory waves detected by the optical fiber sensor 11.

Thus, according to the apparatus for diagnosing deterioration of a pipe in this embodiment, it is not necessary to input oscillatory waves into the pipe 60 by the oscillator 15 of the active sensor 10, which is necessary in the above first embodiment, but it is possible to passively detect oscillatory waves generated in the pipe 60 for some reason or other, to thereby detect the thickness of the pipe 60 and the deterioration and the malfunction of the pipe 60.

Further, with the use of the information relating to the deterioration and the malfunction of the pipe 60, which has been stored in the diagnostic database 33 beforehand, the pipe 60 can be diagnosed in accordance with its size and thickness, which may differ with the industry and the kind. Furthermore, it is possible, not only to calculate the thickness of the pipe 60 so as to diagnose deterioration and malfunction of the pipe 60, but also to judge a lifetime of the pipe 60.

According to the present invention, after oscillatory waves are inputted into the pipe 60 by the oscillator 15 of the active sensor 10, the oscillatory waves generated in the pipe 60 can be actively detected by the optical fiber sensor 11 of the active sensor 10, which is shown in as shown in the above first embodiment (including the alternative examples 1 and 2). Alternatively, oscillatory waves generated in the pipe 60 for some reason or other can be passively detected without inputting oscillatory waves into the pipe 60, which is shown in the second embodiment. Therefore, the deterioration and the malfunction of the pipe 60 can be detected with a high probability.

What is claimed is:

1. An active sensor positioned on an outside of a pipe so as to detect a thickness of the pipe, the active sensor comprising:
    an oscillator to input oscillatory waves into the pipe and scan a frequency of the oscillatory waves within a desired range; and
    an optical fiber sensor mounted on the pipe to detect reflected waves and resonant waves generated in the pipe.

2. The active sensor according to claim 1, wherein
    the oscillator has a permanent magnet positioned so as to generate a magnetic flux in a normal, line direction of a pipe surface, and an electric coil disposed on the permanent magnet on a side of the optical fiber sensor.

3. The active sensor according to claim 1, wherein
the oscillator has a permanent magnet positioned so as to generate a magnetic flux in a normal line direction of a pipe surface, an electric coil disposed on the permanent magnet on a side of the optical fiber sensor, and a holding member that holds the electric coil and the optical fiber sensor in such a manner that the electric coil and the optical fiber sensor are not brought into direct contact with each other.

4. The active sensor according to claim 1, wherein
the oscillator has a pair of permanent magnets positioned so as to generate a magnetic flux in a direction perpendicular to a normal line direction of a pipe surface, and an electric coil disposed between the pair of permanent magnets.

5. The active sensor according to claim 1, wherein
the oscillator has a pair of permanent magnets positioned so as to generate a magnetic flux in a direction perpendicular to a normal line direction of a pipe surface, and an electric coil disposed between the pair of permanent magnets, and a holding member that holds the pair of permanent magnets, the electric coil, and the optical fiber sensor in such a manner that the pair of permanent magnets, the electric coil, and the optical fiber sensor are not brought into direct contact with each other.

6. The active sensor according to claim 1, wherein
the oscillator is formed from an electromagnetic oscillator or a piezoelectric oscillator.

7. The active sensor according to claim 1, wherein
the optical fiber sensor is formed from a fiber-optic Doppler (FOD) sensor that detects a kinetic strain of the pipe, which is generated by the oscillatory waves inputted from the oscillator into the pipe.

8. The active sensor according to claim 1, wherein:
the optical fiber sensor has a circularly or elliptically winding sensing part; and
the oscillator is positioned at a center of the sensing part.

9. The active sensor according to claim 8, wherein
the sensing part of the optical fiber sensor is subjected to a heat-resistant process.

10. The active sensor according to claim 8, wherein
a conductive material is disposed on a surface of the sensing part of the optical fiber sensor.

11. The active sensor according to claim 1, wherein
the optical fiber sensor has an inner diameter not less than 5 mm, and an outer diameter not more than a value that is obtained by adding, to the inner diameter, one half of a wavelength of the oscillatory waves propagating in the pipe.

12. A multi-point active sensor comprising a plurality of active sensors according to claim 1,
wherein the active sensors are linearly arranged or arranged in a matrix.

13. The multi-point active sensor according to claim 12, wherein
the respective active sensors are connected to each other by a connection member having a plasticity or flexibility.

14. A method of diagnosing deterioration of a pipe using the multi-point active sensor according to claim 12, the method comprising the steps of:
inputting oscillatory waves into a pipe by the oscillator of at least one active sensor;
detecting the reflected waves and the resonant waves generated in the pipe by the optical fiber sensor of at least one active sensor; and
calculating a thickness of the pipe by deriving a relationship between a frequency and a vibration strength, based on a frequency of the oscillatory waves inputted by the oscillator into the pipe and an amplitude of the reflected waves and the resonant waves at this frequency detected by the optical fiber sensor.

15. An apparatus for diagnosing deterioration of a pipe, comprising:
the multi-point active sensor according to claim 12;
a waveform analysis unit connected to the respective active sensors, the waveform analysis unit calculating a thickness of a pipe by deriving a relationship between a frequency and a vibration strength, based on a frequency of oscillatory waves inputted by the oscillator of this active sensor into the pipe and an amplitude of the reflected waves and the resonant waves at this frequency detected by the optical fiber sensor of this active sensor;
a diagnostic database storing judgment threshold values relating to the deterioration of the pipe; and
a diagnostic unit connected to the waveform analysis unit and the diagnostic database, the diagnostic unit comparing the thickness of the pipe calculated by the waveform analysis unit with the judgment threshold values stored in the diagnostic database, so as to diagnose the deterioration and the malfunction of the pipe.

16. The apparatus for diagnosing deterioration of a pipe according to claim 15, wherein
the waveform analysis unit calculates the thickness of the pipe by deriving a relationship between a frequency and a vibration strength, based on a frequency of the oscillatory waves inputted into the pipe by the oscillator and an effective value of an amplitude of the reflected waves and the resonant waves or a frequency spectral intensity obtained by Fourier converting the reflected waves and the resonant waves at the frequency detected by the optical fiber sensor.

17. A method for diagnosing deterioration of a pipe using the multi-point active sensor according to claim 12, the method comprising the steps of:
passively detecting oscillatory waves generated in a pipe by the optical fiber sensor of at least one active sensor; and
analyzing the oscillatory waves generated in the pipe and detected by the optical fiber sensor, so as to detect deterioration and malfunction of the pipe.

18. The method for diagnosing deterioration of a pipe according to claim 17, wherein
the oscillatory waves detected by the optical fiber sensors of the respective active sensors are analyzed referring to information relating to deterioration of the pipe, which information having been stored in a diagnostic database beforehand, so as to detect deterioration and malfunction of the pipe.

19. An active sensor positioned on an outside or an inside of a pipe so as to detect a thickness of the pipe, the active sensor comprising:
an oscillator to input oscillatory waves into the pipe and scan a frequency of the oscillatory waves over a desired range; and
an optical fiber sensor mounted on the pipe to detect reflected waves and resonant waves generated in the pipe.

* * * * *